United States Patent [19]

Ihara et al.

[11] 4,278,934
[45] Jul. 14, 1981

[54] ELECTRODE ASSEMBLY FOR A MOISTURE METER

[75] Inventors: Susumu Ihara; Yoshinobu Kashiuchi; Isamu Jinguji, all of Osaka, Japan

[73] Assignee: Sumitomo Electric Industries, Ltd., Osaka, Japan

[21] Appl. No.: 33,408

[22] Filed: Apr. 26, 1979

[30] Foreign Application Priority Data

Apr. 27, 1978 [JP] Japan ............................. 53-58598[U]
Apr. 27, 1978 [JP] Japan ............................. 53-58599[U]

[51] Int. Cl.³ ........................................... G01R 27/26
[52] U.S. Cl. .................................................. 324/61 P
[58] Field of Search ........................... 324/61 P, 61 R; 361/280, 281, 286

[56] References Cited

U.S. PATENT DOCUMENTS

| 2,759,147 | 8/1956 | Stein | 324/61 P |
| 2,774,938 | 12/1956 | Edinborgh | 324/61 R |
| 2,975,361 | 3/1961 | Holaday | 324/61 R X |
| 3,123,751 | 3/1964 | Balsbaugh | 324/61 R X |

FOREIGN PATENT DOCUMENTS 195059  3/1965  Sweden .................................. 324/61 P

*Primary Examiner*—Stanley T. Krawczewicz
*Attorney, Agent, or Firm*—Wenderoth, Lind & Ponack

[57] ABSTRACT

An improved electrode assembly for a moisture meter of the electrostatic capacity type. The electrodes include a high-voltage electrode and a plurality of ground electrodes. The high-voltage electrode is insulated or electrostatically shielded at the base thereof in order to ensure high accuracy of the moisture meter.

2 Claims, 4 Drawing Figures

ELECTRODE ASSEMBLY FOR A MOISTURE METER

BACKGROUND OF THE INVENTION

The present invention relates to an improved electrode for a moisture meter of the type which determines the water content of a powdery or granular material by measuring its electrostatic capacity.

Various methods have been proposed and used for the measurement of moisture which is contained in powdery or granular material. Among the methods used, there is a method which measures the electrostatic capacity of the sample in order to determine the water content. In this method, measuring electrodes, which are connected in parallel with a resonance circuit, are inserted into a sample for measuring the electrostatic capacity between the electrodes as the change in electrostatic capacity in the resonance circuit. Since the electrostatic capacity of the sample is proportional to the water content, the latter can be determined by measuring the former.

For a moisture meter of this type, an electrode has normally been used which includes a high-voltage electrode, a plurality of ground electrodes which are arranged in parallel with the high-voltage electrode, and an insulator to which said electrodes are secured.

The conventional electrode described includes a few drawbacks. First, if the electrode is inserted into the sample, not all the way to the root of the electrodes, but incompletely (because the surface of the sample is not level or for any other reason) the measurement which would result would be lower than the true value.

Second, in the case where drift compensation is performed after actual moisture measurement, if some of the sample remains on the base portion of the electrode, the drift compensation would be inaccurate because of the effect of the remaining sample which accordingly increases the electrostatic capacitance between the electrodes.

Thirdly, the effect of stray capacitance on the measuring results is not negligible.

SUMMARY OF THE INVENTION

It is therefore an object of the present invention to provide an improved electrode for a moisture meter of the type which eliminates the above-described problems, thus ensuring accurate moisture measurement.

BRIEF DESCRIPTION OF THE DRAWINGS

Other objects and advantages of the present invention will become apparent from the following description taken with reference to the accompanying drawings, in which.

Like numerals are employed to designate like or corresponding parts throughout the drawings.

DETAILED DESCRIPTION OF THE INVENTION

Figure 1A:
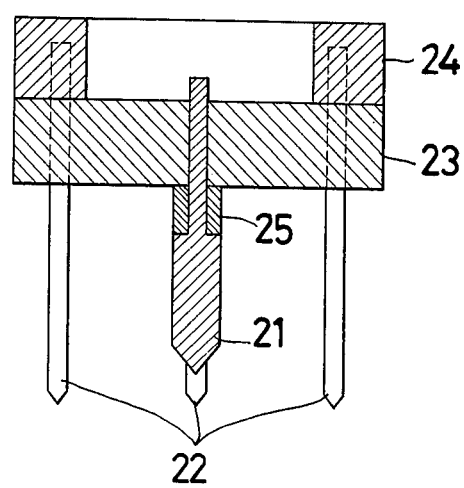
FIG. 1a is a vertical sectional view of a first embodiment of the invention.
Figure 1B:
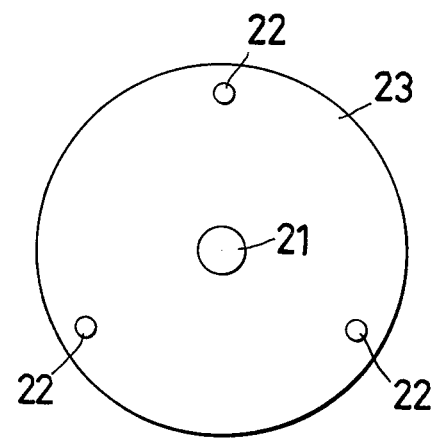
FIG. 1b is a plan view thereof.

Referring to FIGS. 1a and 1b which shows the first embodiment of the invention, there is provided a high-voltage electrode 21, a plurality of ground electrodes 22 which are arranged around and in parallel with the high-voltage electrode, an insulator 23 for holding these two kinds of electrodes in position, a fixing member 24 for the ground electrodes 22, and an insulator 25 which is mounted on the base portion of the high-voltage electrode 21. Preferably, the insulator 25 has a small dielectric constant relative to insulator 23. The ground electrodes 22 are longer than the high-voltage electrode 21 to for minimizing the effect of stray capacitance.

As a result of this arrangement, the electrostatic capacitance between the insulator 25 and the ground electrodes 22, with the sample located therebetween, is considerably smaller than that which occurs between the high-voltage electrode 21 and the ground electrodes 22 of the conventional prior art electrode having an equal amount of the sample present therebetween. Even if the electrode of the FIGS. 1a and 1b is not completely inserted into the sample up to the base portion of the electrodes, the varying effect thereof would be smaller than with the conventional electrode so long as it is inserted to the point where the exposed portion of the high-voltage electrode 21 is completely covered by the sample. Also, any varying effect, due to any of the sample remaining on the insulator 25, on the accuracy of the drift compensation is clearly less than with the conventional prior art electrode.

Figure 2A:
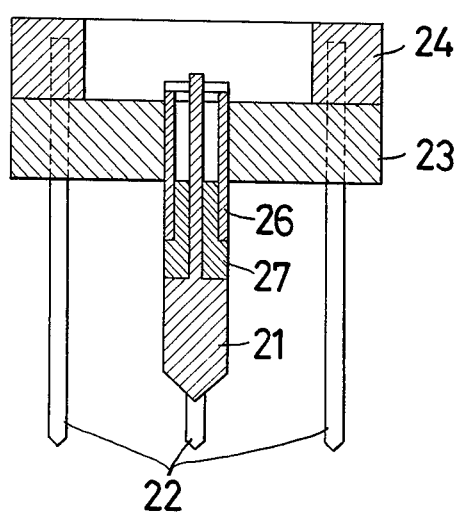
FIG. 2a is a vertical sectional view of a second embodiment of the invention.
Figure 2B:
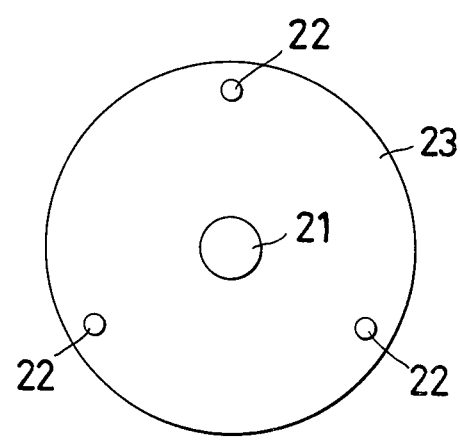
FIG. 2b is a plan view thereof.

FIGS. 2a and 2b illustrate the second embodiment of the present invention which includes the same parts or components as the electrode of FIGS. 1a and 1b except that an insulator 27 is mounted on the base portion of the high-voltage electrode 21 and an electrostatic shield 26 is mounted on the insulator 27 in a way so as to extend through the insulator 23.

This arrangement ensures that the sample which is present between the electrostatic shield 26 and the ground electrodes 22 does not cause an appreciable increase in the electrostatic capacitance between the high-voltage electrode and the ground electrodes. Therefore, in this embodiment, also, any varying effect of the incomplete insertion of the electrode into the sample and of the sample adhering to the base portion of the electrodes is much smaller than with the conventional prior art electrode.

Both of the embodiments ensure a stable and accurate measurement of the water content in a sample for long periods of time. Stray capacitance can be minimized because the high-voltage electrode is shorter than the earth electrodes.

A plurality of the high-voltage electrodes can be employed instead of one. In that case too, the above-described effects can be expected by providing an insulator 25 or an electrostatic shield 26 at the base portion of each high-voltage electrode.

Although the present invention has been described with reference to the preferred embodiments, it is understood that various changes or variations can be made which fall within the scope of the present invention.

What we claim:
1. An electrode assembly for an electrostatic moisture meter of the electrostatic capacity type for determining the moisture content of powdery or granular material, said assembly comprising:
   a primary insulator;
   at least one secondary insulator mounted on the base of at least one high-voltage electrode in the form of a rod, said at least one secondary insulator and at least one high-voltage electrode mounted in said primary insulator and extending outwardly therefrom;

a plurality of ground electrodes in the form of rods, said ground electrodes being mounted in said primary insulator at locations spaced around said at least one high-voltage electrode, and said ground electrodes being longer than said at least one high-voltage electrode; and an electrostatic shield mounted on said at least one secondary insulator and extending through said primary insulator for preventing an appreciable increase in electrostatic capacitance between said at least one high-voltage electrode and said ground electrode.

2. An electrode assembly as in claim 1 wherein said at least one secondary insulator has a small dielectric constant relative to said primary insulator.

* * * * *